US011986246B2

(12) United States Patent
Roldan et al.

(10) Patent No.: US 11,986,246 B2
(45) Date of Patent: May 21, 2024

(54) METHOD TO DETERMINE BONE PLACEMENT IN A ROBOT WORKSPACE

(71) Applicant: THINK SURGICAL, INC., Fremont, CA (US)

(72) Inventors: Jay Roldan, Fremont, CA (US); Min Yang Jung, Fremont, CA (US); Feimo Shen, Fremont, CA (US); Muhammad Afnan, Fremont, CA (US); Barry Voorhees, Fremont, CA (US); Micah Forstein, Fremont, CA (US); CJ Geering, Fremont, CA (US); Koteswara Ruvva, Fremont, CA (US); Joel Zuhars, Fremont, CA (US)

(73) Assignee: Think Surgical, Inc., Fremont, CA (US)

(*) Notice: Subject to any disclaimer, the term of this patent is extended or adjusted under 35 U.S.C. 154(b) by 229 days.

(21) Appl. No.: 16/911,709

(22) Filed: Jun. 25, 2020

(65) Prior Publication Data

US 2020/0405394 A1     Dec. 31, 2020

Related U.S. Application Data

(60) Provisional application No. 62/866,348, filed on Jun. 25, 2019.

(51) Int. Cl.
*A61B 34/10* (2016.01)
*A61B 17/16* (2006.01)
*A61B 34/00* (2016.01)
*G16H 20/40* (2018.01)
(Continued)

(52) U.S. Cl.
CPC .......... *A61B 34/10* (2016.02); *A61B 17/1626* (2013.01); *A61B 17/1675* (2013.01); *A61B 34/25* (2016.02); *A61B 34/74* (2016.02); *A61B 34/76* (2016.02); *G16H 20/40* (2018.01); *G16H 40/63* (2018.01); *G16H 50/50* (2018.01); *A61B 2017/1602* (2013.01);
(Continued)

(58) Field of Classification Search
CPC ............ A61B 17/1626; A61B 17/1675; A61B 2017/1602; A61B 2034/104; A61B 2034/105; A61B 2034/107; A61B 2034/2051; A61B 2034/2055; A61B 2034/741; A61B 34/10; A61B 34/25; A61B 34/30; A61B 34/74; A61B 34/76; A61B 90/13; G16H 20/40; G16H 40/63; G16H 50/50
See application file for complete search history.

(56) References Cited

U.S. PATENT DOCUMENTS 5,086,401 A * 2/1992 Glassman ................. A61F 2/46
606/88
2006/0142657 A1* 6/2006 Quaid ..................... A61B 90/37
600/424

(Continued)

*Primary Examiner* — Manuchehr Rahmjoo
(74) *Attorney, Agent, or Firm* — MaxGoLaw PLLC

(57) ABSTRACT

A method and system are provided to determine an optimal placement with respect to position and orientation for one or more bones in a workspace of a robot to improve robotic cutting and maximize the robot workspace during a robotic surgical procedure. The method is additionally useful to aid a user in positioning and orienting the bones in the operating room at the determined position and orientation.

19 Claims, 6 Drawing Sheets

(51) Int. Cl.
  *G16H 40/63* (2018.01)
  *G16H 50/50* (2018.01)
(52) U.S. Cl.
  CPC ... *A61B 2034/104* (2016.02); *A61B 2034/105* (2016.02); *A61B 2034/107* (2016.02); *A61B 2034/741* (2016.02)

(56) References Cited

U.S. PATENT DOCUMENTS

2007/0219561 A1* 9/2007 Lavallee ............... A61B 90/36
  606/90
2010/0153081 A1* 6/2010 Bellettre ............... G06T 17/20
  715/764

* cited by examiner

METHOD TO DETERMINE BONE PLACEMENT IN A ROBOT WORKSPACE

RELATED APPLICATIONS

This application claims priority benefit of U.S. Provisional Application Ser. No. 62/866,348 filed 25 Jun. 2019, the contents of which are hereby incorporated by reference.

TECHNICAL FIELD

The present invention generally relates to the field of robotic orthopedic surgery, and more particularly to a method to determine the optimal placement for one or more bones relative to a robotic surgical arm to improve robotic cutting

BACKGROUND

Robotic surgical devices are gaining popularity as a tool to pre-operatively plan and precisely execute the plan to ensure an accurate final position and orientation of a prosthetic within a patient's bone that can improve long term clinical outcomes and increase the survival rate of a prosthesis. Conventional interactive pre-operative planning software generates a three dimensional (3-D) model of the patient's bony anatomy from a computed tomography (CT) or magnetic resonance imaging (MRI) image dataset of the patient. A set of 3-D computer aided design (CAD) models of the manufacturer's prosthesis are pre-loaded in the software that allows the user to place the components of a desired prosthesis to the 3-D model of the bony anatomy to designate the best fit, position, and orientation of the prosthesis to the bone. The surgical plan data may include a volume of tissue for modification that is defined relative to the anatomy such as a set of points in a cut-file to remove bone, or a set of virtual boundaries to sculpt the bone. The user can then transfer the pre-operative planning data to the robotic device to assist the surgeon intra-operatively in executing the plan.

To perform a joint replacement procedure with a robotic system, the correct positioning of the robot with respect to the patient is critical. Currently, a moveable base of the robotic system is manually maneuvered next to the target anatomy and fixed into a position using a braking mechanism on the moveable base. The position and orientation (POSE) of the bone is then registered to the surgical plan and the surgical system. After the respective coordinates are known, the robotic system determines if an end-effector tool of the robot can perform a surgical task (i.e., execute the surgical plan) on the anatomy. All of the points or boundaries in the task should be within the workspace of the robot and hence they should be reachable by the robot. In other words, the end-effector tool needs to reach all of the points or boundaries designated in the surgical plan with respect to the target anatomy.

The primary problem with the current approach is there is limited a priori information for the optimal position for the base. Therefore, if the robotic system determines the end-effector tool is unable to perform the surgical task with the base already fixed relative to the patient, the base may need to be repositioned and the bone re-registered. In addition, there is no guarantee that the new position for the base is suitable to perform the surgical task. There is also the possibility where the position of the base with respect to the anatomy changes causing the designated points or boundaries to also change within the workspace of the robot. This becomes more important in cases of total knee arthroplasty (TKA) in which the end-effector tool is reoriented several times. All of these problems can greatly increase the operating time, especially if the target anatomy needs to be fixed to the robotic system (e.g., see robotic-bone fixation as described in U.S. Pat. No. 5,086,401).

In addition, even after the bone has been positioned within the workspace of the robot workspace, the POSE of the bone may be inefficiently positioned to optimize robotic cutting. The POSE of the bone also determines the arm and end-effector orientations to accurately cut the bone according to the plan. In some instances, the arm and end-effector orientations may cause the side of the cutter, or the side of a sleeve surrounding and supporting the cutter, to contact the bone. Due to safety requirements, a force sensor monitors the forces experienced on the cutter or sleeve and any force experienced above a threshold level causes the arm to stop. This often occurs when the side of the cutter or sleeve contacts a portion of the bone. There is currently no method to aid the surgeon in positioning the bone to avoid these force freezes.

Thus, there exists a need in the art for a method to determine an optimal position and orientation for one or more bones in a workspace of a robot to improve robotic cutting. There is a further need to aid a user in positioning the bones in the operating room at the determined position

SUMMARY OF THE INVENTION

A method is provided for determining an optimal placement for one or more bones in a workspace of a robot during a robotic surgical procedure. The method includes providing one or more cut-files for the robot to remove a volume of bone from the one or more bones to receive an implant thereon, executing a cutting simulation of one or more cut-files on a computer having a kinematic model of the robot, and repeating the cutting simulation for a plurality of cut-file workspace positions and orientations (POSEs). The method further includes determining one or more cut-file workspace POSEs that had a successful kinematic completion of the simulation of the cut-file, where a successful kinematic completion is characterized by: (i) an end-effector of the robot reaching all points along a plurality of cut paths defined in the cut-file; and (ii) joint positions and velocity limits of a robot arm of the robot are within operating range of the robot. The method concludes with positioning the one or more bones in the workspace of the robot according to one of the cut-file workspace POSEs that had a successful kinematic completion of the simulation of the cut-file.

A method is provided to determine an optimal placement for one or more bones in a workspace of a robot. The method includes generating a first bone model of a first bone, a second bone model of a second bone, and a range-of-motion model of the first bone model relative to the second bone model, where the first bone and the second bone are part of a joint, and providing one or more cut-files for the robot to remove a volume of bone in the first bone and the second bone to receive one or more implants. The method further includes providing a computer with: (i) a kinematic model of the robot, (ii) a virtual model of a robot end-effector, (iii) the first bone model and the second bone model, and (iv) the range-of-motion model of the first bone model relative to the second bone model; where for each orientation of the first bone model relative to the second bone model in the range-of-motion model, the computer performs a first set of simulations simulating the end-effector virtual model executing the one or more cut-files on the first bone model and the second bone model. Based on the simulations, one or more orientations of the first bone model relative to the second bone model having a successful non-collision completion of the cut-file is determined, where a successful non-collision completion is characterized by a portion of the end-effector virtual model not inadvertently interfering or contacting an unintended portion of the first bone model or the second bone model.

A computer-assisted surgical system is provided for implementing the aforementioned methods for optimal placement for one or more bones in a workspace of a robot. The system includes a computer-assisted surgical device having an end-effector, and a computing system having operational data to be executed by the surgical device to remove bone according to a surgical plan based on the positioning of a patient's bones.

BRIEF DESCRIPTION OF THE DRAWINGS

The present invention is further detailed with respect to the following drawings that are intended to show certain aspects of the present of invention, but should not be construed as limit on the practice of the invention, wherein:

FIG. 5B depicts the end-effector cutting bone at a first point in the cut-file, and FIG. 5C depicts the end-effector cutting bone at a second point in the cut-file.

DETAILED DESCRIPTION

Figure 1:
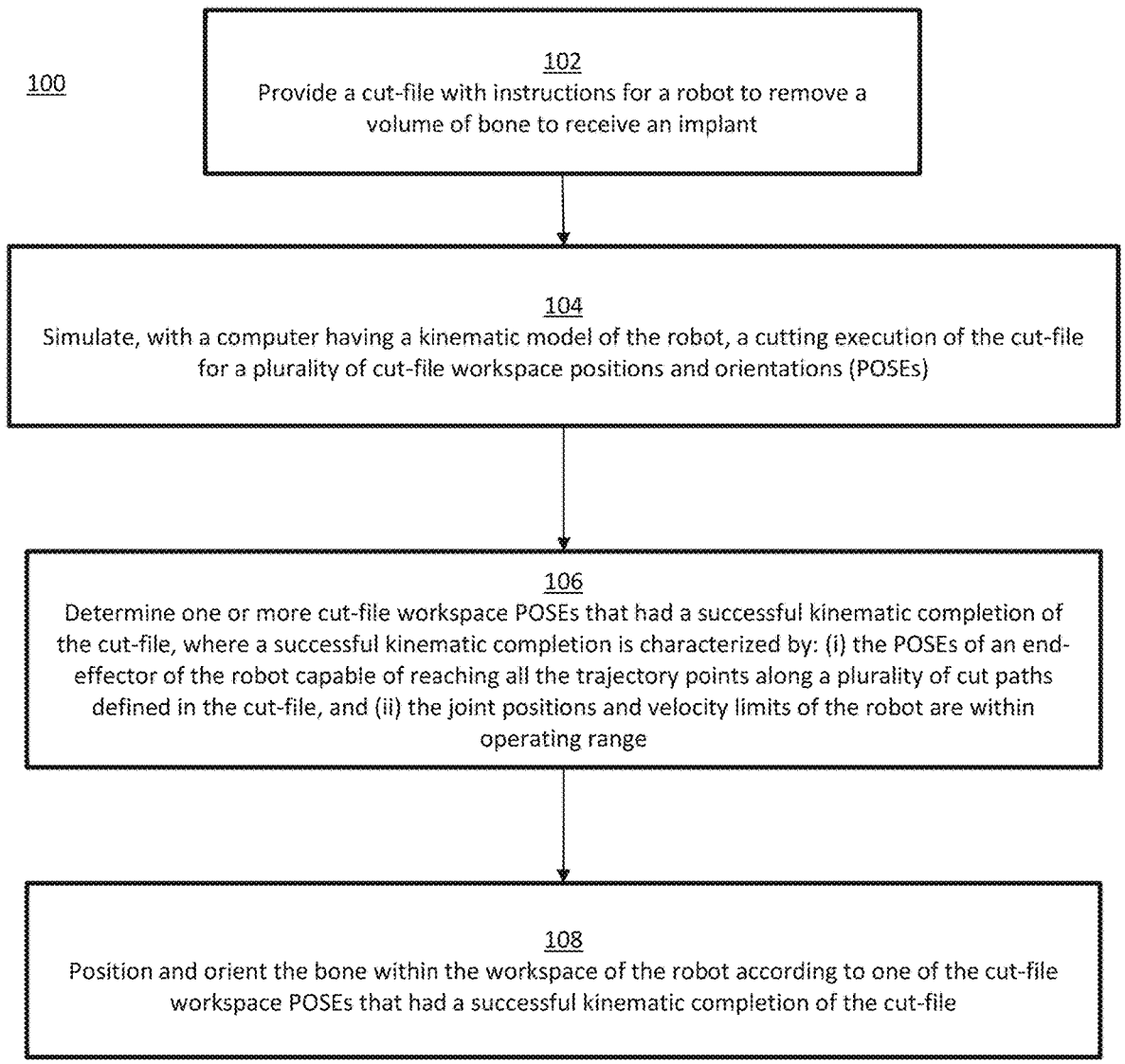
FIG. 1 depicts a flow chart methodology to determine optimal bone placement in the workspace of a robot based on the kinematic restraints of the robot in accordance with embodiments of the invention.

The present invention has utility as a method to determine an optimal position and orientation for one or more bones in a workspace of a robot to improve robotic cutting. The method is additionally useful to aid a user in positioning and orienting the bones in the operating room at the determined position and orientation.

The present invention will now be described with reference to the following embodiments. As is apparent by these descriptions, this invention can be embodied in different forms and should not be construed as limited to the embodiments set forth herein. For example, features illustrated with respect to one embodiment can be incorporated into other embodiments, and features illustrated with respect to a particular embodiment may be deleted from that embodiment. In addition, numerous variations and additions to the embodiments suggested herein will be apparent to those skilled in the art in light of the instant disclosure, which do not depart from the instant invention. Hence, the following specification is intended to illustrate some particular embodiments of the invention, and not to exhaustively specify all permutations, combinations and variations thereof.

Further, it should be appreciated that although the systems and methods described herein make reference to the proximal femur, the systems and methods may be applied to other bones and joints in the body illustratively including the hip, ankle, elbow, wrist, skull, and spine, as well as revision of initial repair or replacement of any of the aforementioned bones or joints.

Unless otherwise defined, all technical and scientific terms used herein have the same meaning as commonly understood by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference in their entirety.

Unless indicated otherwise, explicitly or by context, the following terms are used herein as set forth below.

As used in the description of the invention and the appended claims, the singular forms "a," "an" and "the" are intended to include the plural forms as well, unless the context clearly indicates otherwise.

Also, as used herein, "and/or" refers to and encompasses any and all possible combinations of one or more of the associated listed items, as well as the lack of combinations when interpreted in the alternative ("or").

As used herein, the term "digitizing" refers to the collecting, measuring, and/or recording of physical points in space with a digitizer.

As used herein, the term "pre-operative bone data" refers to bone data used to pre-operatively plan a procedure before making modifications to the actual bone. The pre-operative bone data may include one or more of the following. A patient's actual exposed bone prior to modification, an image data set of a bone, a virtual generic bone model, a physical bone model, a virtual patient-specific bone model, or a set of data collected directly on a bone intra-operatively commonly used with imageless computer-assist devices.

As used herein, a "cut-file" refers to a software file having set of instructions to autonomously or haptically control a robotic system. The set of instructions illustratively include cut paths, points, virtual boundaries, velocities, accelerations, spindle speeds, feed rates, and any combination thereof to autonomously or haptically control the robot.

As used herein, the term "registration" refers to the determination of the POSE and/or coordinate transformation between two or more objects or coordinate systems such as a computer-assist device, a bone, pre-operative bone data, surgical planning data (e.g., an implant model positioned relative to pre-operative bone data, a cut-file defined relative to an implant model and/or pre-operative bone data, virtual boundaries defined relative to an implant model and/or pre-operative bone data, virtual planes defined relative to an implant model and/or pre-operative bone data, or other cutting parameters associated with or defined relative to an implant model and/or the pre-operative bone data), and any external landmarks (e.g., a fiducial marker array) associated/attached with the bone, if such landmarks exist. Methods of registration known in the art are described in U.S. Pat. Nos. 6,033,415; 8,010,177; 8,036,441; 8,287,522; and 10,537,388.

As used herein, the term "real-time" refers to the processing of input data within milliseconds such that calculated values are available within 2 seconds of computational initiation.

As used herein, a "robotic surgical system" refers to any system (or device) requiring computer control of an end-effector to aid in a surgical procedure. Examples of a robotic surgical device include active and haptic, 1 to N degree(s) of freedom (DOF) hand-held surgical devices and systems, autonomous serial-chain manipulator systems, haptic serial chain manipulator systems, parallel robotic systems, master-slave robotic systems, etc., as described in, for example, U.S. Pat. Nos. 5,086,401; 7,206,626; 8,876,830; 8,961,536; 9,707,043; and U.S. Pat. Patent Application Publication 2018/0344409, which patents, patent publications and patent applications are hereby incorporated herein by reference. An exemplary embodiment of a robotic surgical system is described below.

Figure 2A:
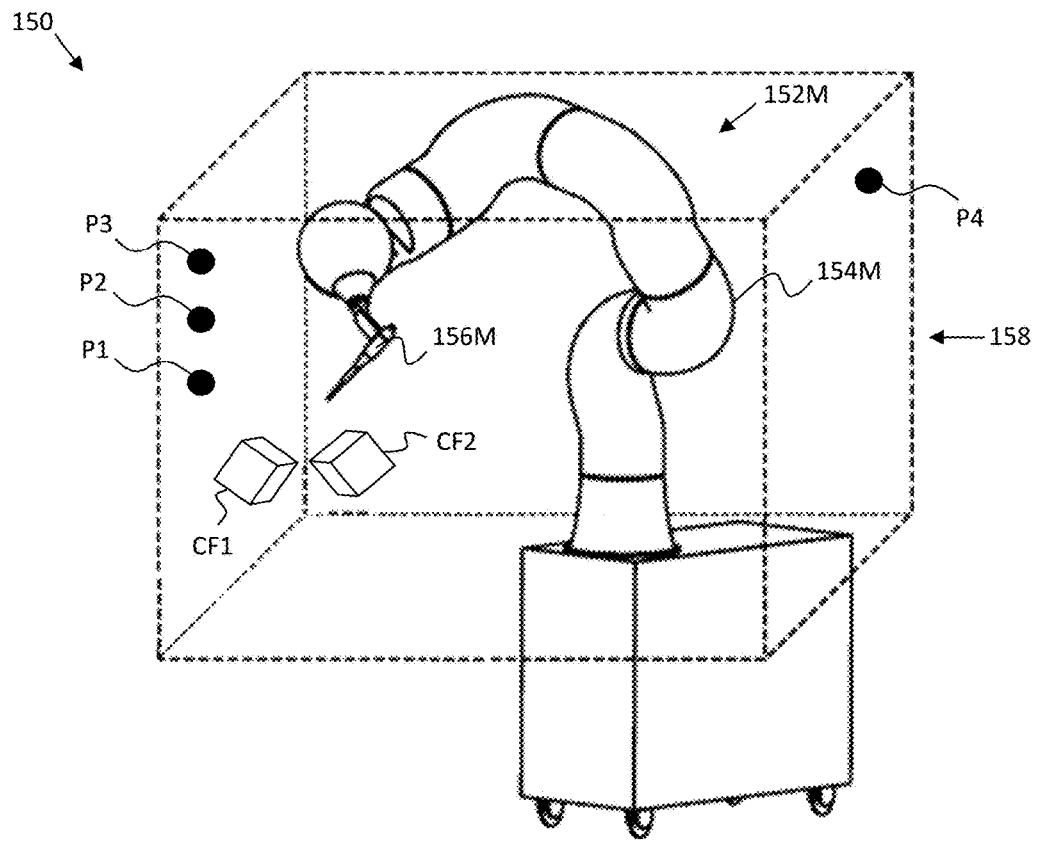
FIG. 2A depicts a virtual robot environment to perform a set of simulations of a cut-file in accordance with embodiments of the invention.

Method to Determine Optimal Bone Placement Based on the Kinematic Constraints of a Robot With reference now to the drawings, FIG. 1 depicts an embodiment of a method 100 to determine an optimal placement for one or more bones in a workspace of a robot to improve robotic cutting and maximize the robot workspace. The method includes the following steps. A cut-file is provided with instructions for a robot to remove a volume of bone to receive an implant (Block 102). A simulation of cutting based on the cut-file is executed on a computer having a kinematic model of the robot (an example of which is shown in FIG. 2A), where the simulation is repeated for a plurality of cut-file workspace positions and orientation (POSEs) (Block 104). One or more cut-file workspace POSEs that had a successful kinematic completion of the simulation of the cut-file is determined, where a successful kinematic completion is characterized by: (i) an end-effector of the robot reaching all trajectory points along a plurality of cut paths defined in the cut-file; and (ii) the joint positions and velocity limits of the robot arm are within operating range (Block 106). In the operating room, the bone is positioned and oriented in the workspace of the robot according to one of the cut-file workspace POSEs that had a successful kinematic completion of the simulation of the cut-file (Block 108). Specific embodiments of the method 100 are further described below.

A cut-file is provided to remove a volume of bone to receive an implant (Block 102). The cut-file may be generated based on the geometry of the implant, the geometry of the bone models, a planned position of the implant models relative to the bone models, or a combination thereof using computer-aided manufacturing (CAM) techniques. One or more cut-files may be generated where each cut-file provides a set of instructions for removing different areas of bone. Further, more than one cut-file may be generated for removing bone in two or more bones, where the bones are part of a joint (e.g., a femur and a tibia of a knee joint). The generated cut-file(s) may be subsequently provided to another software program illustratively including a pre-operative planning software program or a robot simulation software program.

With the provided cut-file(s), a series of simulations are performed to determine one or more positions and orientations for one or more bones in the robot workspace to improve robotic cutting (Block 104). The simulations are performed on a computer having robot simulation software that is programmed with a kinematic model of the robot to simulate the robot's movements as defined in the cut-file. These simulations are repeated for a plurality of cut-file POSEs in a virtual workspace of the robot to determine where in the workspace the robot can successfully complete the cut-file as further described with reference to FIG. 2A. With reference to FIG. 2A, an example of a robotic virtual environment 150 is shown. The virtual environment 150 depicts a virtual model of a robotic system 152M having a robot arm 154M controlling an end-effector 156M; the workspace 158 of the robot as denoted by the dotted cube; and a first cut-file CF1 and a second cut-file CF2, which may represent the POSEs of the bone in the workspace 158. As a side note, the simulations described herein considered the POSE of the cut-files equal to the POSE of the bone for the purposes of simplification, but they are not necessarily equivalent in all circumstances. Generally there is a different transformation between the bone and the cut-file, which may be considered in other embodiments of the present invention. With the simulation software, the cutting execution of the cut-file are simulated for a plurality of cut-file POSEs in the robot's workspace 158 to determine which POSEs result in a successful completion of the set of instructions. For example, the first cut-file CF1 and second cut-file CF2 may be virtually positioned with respect to the robot at a first position P1 in the robot workspace 158. At position P1, the cut-files (CF1 and CF2) are simulated over a range of cut-file orientations. That is, at position P1, a first simulation is performed with the cut-files (CF1 and CF2) at a first orientation, and then a second simulation is performed with the cut-files (CF1 and CF2) at a second orientation, and so on for a plurality of orientations as permitted by the degrees-of-freedom (e.g., pitch and roll) of the end-effector 156M. In some embodiments, the simulations are performed on two or more cut-files (e.g., CF1 and CF2) simultaneously to simplify the process, while in other embodiments the simulations are performed for each cut-file (or bone) separately. Performing the simulations for each cut-file separately allows the creation of the orientation space (as described below) for each bone and/or cut-file separately. The orientation space needs to be created for each cut-file (or bone) otherwise the successful and unsuccessful cut-file POSEs might not be represented correctly and information may be lost.

In a particular inventive embodiment, the above range of orientations of the cut-files may be further limited to the expected ranges-of-motion between the two bones in the joint. For instance, at position P1, a first simulation is performed with the two cut-files in full extension, then a second simulations with the cut-files flexed by 2 degrees, and so on until the two cut-files are oriented at an expected maximum flexion angle. Alternatively, the range-of-motion between the two bones may be accounted for by using an optimization constraint after the simulations are complete, where the optimization constraint identifies and labels cut-file POSEs outside the bones range-of-motion as invalid or unsuccessful.

After the simulations are completed at position P1 over the range of orientations, the cut-files (CF1 and CF2), either simultaneously or separately, are positioned at a new position (e.g., P2, P3, P4) and the process is repeated. For each simulation, the simulation software determines which cut-files had a successful kinematic completion of the cut-file as characterized by: (i) the end-effector 156 capable of reaching all of the trajectory points (or virtual boundaries) along a plurality of cut paths defined in the cut-file, and (ii) the joint positions and velocity limits of the robot arm 154 are within operating range.

Figure 2B:
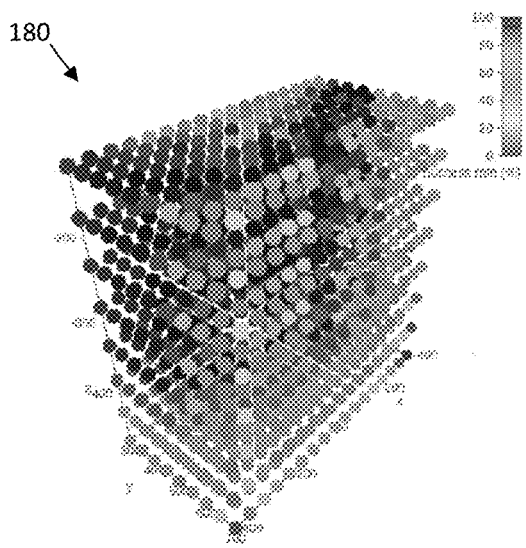
FIG. 2B depicts a workspace map detailing the ratios of successful kinematic completions of a cut-file in accordance with embodiments of the invention.
Figure 2C:
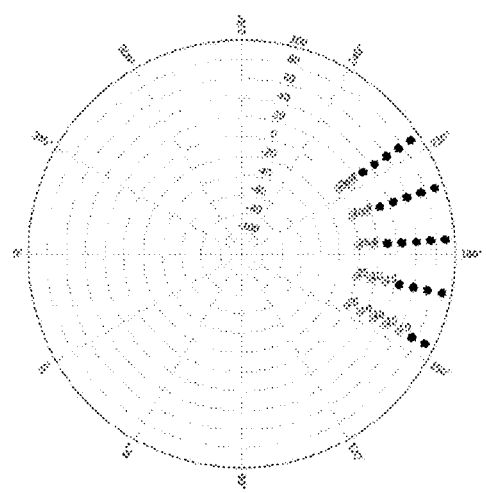
FIG. 2C depicts a graph detailing the ratios of successful kinematic completions of a cut-file for different starting orientations of an end-effector in accordance with embodiments of the invention.

From the data acquired from the simulations, a workspace map 180 is generated as shown in FIG. 2B. The robot workspace map 180 is a discretization of the robot workspace 158 that contains information about the success rate of a specific cut-file within the workspace 158. Each discrete position (data point) in the map represents a cutfile start position. A success rate of a data point means the number of cut-file orientations with a successful kinematic cut completion over the number of cut-file orientations tested. FIG. 2C depicts a sample orientation space (roll and pitch space) of one data point, where the black dots represent orientations with a successful cut completion, and the gray dots represent failed orientations.

To identify an optimal bone location from the data in the workspace map 180 the following method may be performed. One method puts more emphasis on the volume of feasible locations for the bones. A value is assigned to each data point (i) based on its success rate and the success rate of its immediate neighbors using equation 1:

$$M_i = \frac{S_i}{2} + \frac{1}{2}\sum w_k S_k, \quad \text{(EQ. 1)}$$
$$\text{where } w_k = \frac{2}{N_{max}} - \frac{d_k}{d_m}$$

where $M_i$ is the measure of feasible volume of data point i, $S_i$ is the success rate of data point i, $w_k$ is the weight of neighbor k based on its distance from data point i, $S_k$ is the success rate of neighbor k, $d_k$ is the distance of neighbor k from data point i, $d_t$ is the sum of immediate neighbor distances from data point i, and $N_{max}$ is the maximum number of immediate neighbors. The data point with the highest $M_i$ closest to the center of the dexterous workspace is chosen as the optimal bone location.

In the instance of a total knee arthroplasty, there is at least one cut-file for each bone (femur and tibia) and possibly two or more cut-files per bone. To determine the optimal location to accommodate each of these cut-files, the following is performed utilizing the data in the workspace map 180. For cut-files on the same bone, the intersection of the orientation space of each data point is found (if the simulation is performed on two or more cut-files on the same bone simultaneously then the intersection does not need to be found). An approximate transformation (Trans) between the femur and tibia cut-files is identified. A feasibility measure $M_f$ is calculated for all the data points in the femur workspace map (f standing for femur), where the feasibility measure is a measure that scores each POSE in the workspace map that represents the volume of feasible locations for a cutting POSE. An optimal orientation $R_f$ of the femur workspace map is identified for each data point. Then, for each data point $P_f$ in femur workspace map, an associated point $P_t$ and orientation $R_t$ in tibia space is located using the transformation (Trans) (t standing for tibia). A feasibility measure $M_t$ of $P_t$ at orientation $R_t$ is calculated. The feasibility of both the femur and tibia points are scored using $M_k = w_f * m_f + w_t * m_t$. Based on the score, the optimal placement for the bones is located by determining max $M_k$.

The optimal bone placement calculations may further include the following. To calculate the optimal bone placement for a single bone, the optimal POSE 'X' may be calculated with the following equation (Eq. 2) based on the results of an intersected workspace map for cut-files on the same bone.

$$X = \text{argmax}\left(\alpha m_T + \beta\left(1 - \frac{d_T}{d_{max}}\right)\right) \quad \text{(Eq. 2)}$$

where $\alpha$ and $\beta$ are weights, $d_T$ is the distance of the data point T from the position with maximum dexterity, and $d_{max}$ is the maximum distance from the position with maximum dexterity in the workspace map.

To identify the POSE of the knee that is composed of femur and tibia bone, the cut-files on the same bones are intersected as above first if the simulations were NOT performed on two or more cut-files simultaneously. This generates two workspace maps in two spaces, in femur space and in tibia space. The feasibility measure of the data points in femur space are calculated. For each femur data point an associated tibia data point is located at some transformation relative to the femur. Since the tibia is attached to the femur, its movement is constrained to rotations around the axis that connects the two bone (knee flexion) and because during surgical operation the tibia is detached from the femur, the tibia or femur may be displaced within a plane that is formed by the two mechanical axes of the bones. Given this, a feasibility measure for the tibia is calculated different than the femur in that the data points and orientations that are less likely possible to be achieved in the OR are weighted lower. This ensure that the feasibility measure accounts only for bone POSEs that are anatomically possible.

To calculate the tibia feasibility measure, the POSEs that are off from the anatomical constraints are weighted lower. Each associated data points in the tibia space are identified based on a relative transformation from the suggested POSE from the femur data space. The orientation spaces of the tibia are narrowed down to three roll values, and its center values is based on the suggested optimal roll value of its associated femur data point. For example, if the femur data point suggested an optimal roll value of 0 degrees and the relative transformation to tibia space involves a roll rotation of 180 degrees, then the tibia data point's orientation space is trimmed to 3 roll values centered at 180 degrees. This is because the tibia bone has minimal orientation mobility around the z-axis (longitudinal or mechanical axis of the bone) with respect to the femur even if it was detached. To accomplish the said constraint, the success rates of the tibia workspace map are recalculated as follows with equation 3:

$$S_t = \frac{0.1(\theta_{pmaxL} - \theta_{pminL}) + 0.1(\theta_{pmaxR} - \theta_{pminR}) + 0.8((\theta_{pmaxM} - \theta_{pminM})}{(\theta_{pmaxRange})} \quad \text{(Eq. 3)}$$

where $S_t$ is the new success rate based on anatomical constraint, $\theta_{pminL}$ and $\theta_{pmaxL}$ are the minimum and maximum valid pitch range to the left of the center roll value respectively, $\theta_{pmaxR}$ and $\theta_{pmaxR}$ are the minimum and maximum valid pitch range to the right center roll value respectively, and $\theta_{pmaxRange}$ is the maximum range of pitch of the orientation space.

Positional deviations of the tibia from the femur along the y-axis of the world frame are also weighted lower due to the same reason mentioned above. The tibia feasibility measure, $m_t$ based on anatomical constraint is the sum of weighted success rates where the weights are based on deviations from anatomically possible poses with respect to the femur. The farther the distance from an anatomically possible POSE, the lower its assigned weight. Equation 4 below is used for this calculation:

$$M_t = A \frac{\sum S_{tM}}{N_{tM}} + B \frac{\sum S_{tLR}}{N_{tLR}} \quad \text{(Eq. 4)}$$

Here, $S_{tM}$ are the success rates of immediate neighbor data points that are within anatomical constraints, $N_{tM}$ is the total number of immediate neighbor data points within anatomical constraints, $S_{tLR}$ are the success rate of immediate neighbor data points outside of the anatomical constraints, A is weight, B is a weight, and $N_{tLR}$ is the total number of immediate neighbor data points outside of the anatomical constraints.

The knee (combination of femur and tibia) space is generated based on the location of the data point of femur and tibia spaces. Its feasibility measure, $M_k$ is a combined weighted feasibility measure of both femur ($M_f$) and tibia ($M_t$) spaces and it is formulated as $M_k = w_f * m_f + w_t * m_t$ where $w_f$ and $w_t$ are the femur and tibia feasibility measure weights respectively. Once the feasibility measure is calculated, the optimal placement/POSE 'X' for the knee may be calculated.

In the operating room (OR), a user is guided to position and orient the bone(s) in the workspace of the robot via a graphical user interface (GUI). The GUI may display the determined optimal placement relative to a representation of the robot to help guide the user in positioning the bones. If the bones are tracked, virtual bone models may be displayed on the GUI, where the position of the virtual bone models relative to a representation of the robot is displayed and updated in real-time as the user positions the actual bones in the workspace. Other guiding mechanisms may include a projected laser in the workspace of the robot, tracked tactile or haptic gloves, holograms, or mechanical hardware (e.g., rods, bars, arms, brackets, frames) that may be attached to the surgical robot to indicate the optimal placement for the bones.

Figure 3:
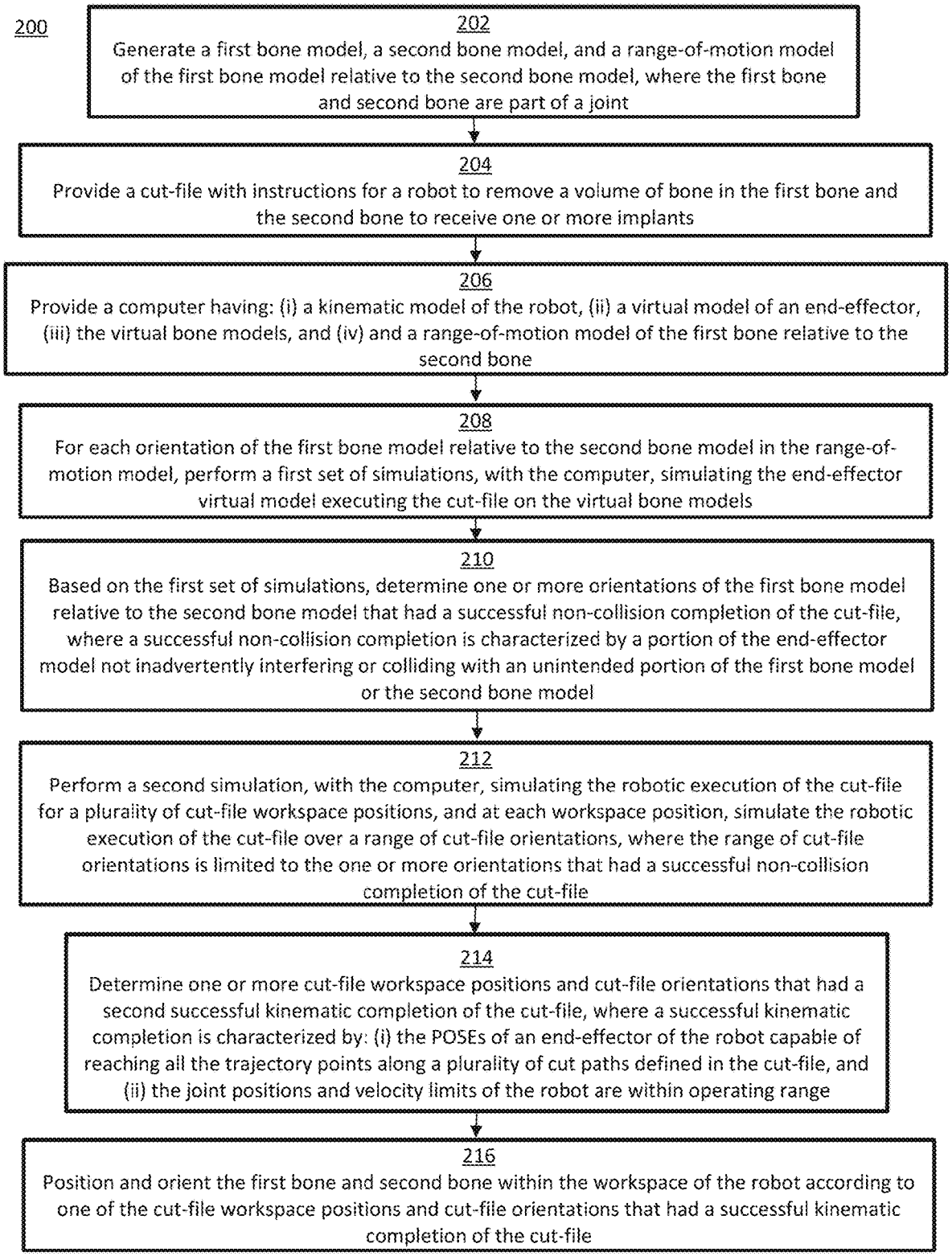
FIG. 3 depicts a method to determine optimal bone placement in the workspace of a robot based on the non-collision of an end-effector with a bone and the kinematic restraints of a robot in accordance with embodiments of the invention.

Method to Determine Optimal Bone Placement Based on a Non-Collision of an End-Effector with a Bone and the Kinematic Constraints of a Robot With reference now to FIG. 3, a particular embodiment of a method 200 to determine an optimal position for one or more bones in a workspace of a robot to improve robotic cutting and maximize the robot workspace is shown. The method includes the following steps. A first bone model of a first bone, a second bone model of a second bone, and a range-of-motion model of the first bone model relative to the second bone model is generated, where the first bone and second bone are part of a joint (Block 202). One or more cut-files are provided for a robot to remove a volume of bone in the first bone and the second bone to receive one or more implants (Block 204). A computer is provided having: (i) a kinematic model of the robot, (ii) a virtual model of a robot end-effector, (iii) the first bone model and the second bone model, and (iv) the range-of-motion model of the first bone model relative to the second bone model (Block 206). For each orientation of the first bone model relative to the second bone model in the range-of-motion model, the computer performs a first set of simulations simulating the end-effector virtual model executing the one or more cut-files on the first bone model and the second bone model (Block 208). Based on the simulations, one or more orientations of the first bone model relative to the second bone model having a successful non-collision completion of the cut-file is determined, where a successful non-collision completion is characterized by a portion of the end-effector virtual model not inadvertently interfering or contacting an unintended portion of the first bone model or the second model (Block 210). The computer then performs a second set of simulations simulating the robotic execution of the cut-file for a plurality of cut-file workspace positions, and at each workspace position, the robotic execution of the cut-file is simulated over a range of cut-file orientations, where the range of cut-file orientations is limited to the one or more orientations that had a successful non-collision completion of the cut-file (Block 212). One or more cut-file positions and cut-file orientations is determined that had a successful kinematic completion of the cut-file, where the successful kinematic completion is characterized by: (i) the end-effector of the robot capable of reaching all trajectory points in the cut-file, and (ii) the joint positions and velocity limits of the robot are within operating range (Block 214). Finally, in the operating room, the first bone and second bone are positioned within the workspace of the robot according to one of the cut-file workspace positions and cut-file orientations that had a successful kinematic completion of the cut-file (Block 216). Specific embodiments of the method 200 are further described below.

The first bone and the second bone are part of a patient's joint, such as the distal femur and proximal tibia to form the knee joint, or the proximal femur and pelvis to form the hip joint. It should be appreciated that other bones forming joints in the body are likewise applicable illustratively including the ankle joint, shoulder joint, elbow joint, and consecutive vertebra. The first bone model of the first bone and the second bone model of the second bone are generated using techniques known in the art. For example, an image data set of the patient's bones may be acquired with an imaging modality illustratively including computed tomography (CT), magnetic resonance imaging (MRI), ultrasound, laser or other 3-D or 2-D scans, or X-rays. From the image data, a 3-D virtual model of the bones are generated using 3-D medical image processing software.

With the first bone model and the second bone model, a user may plan the surgical procedure using a pre-operative planning software program. The planning software program may include a library of implant models the user may select and position relative to the bone models to designate the best fit, fill, and/or alignment for the final implants on the bone. In a particular embodiment, the planning software includes widgets or tools to custom design an implant for a particular bone. The plan is then saved and/or transferred to a robotic system, which executes one or more cut-files to prepare the bones accordingly. The cut-files may be generated based on the geometry of the implant, the geometry of the bone models, a planned position of the implant models relative to the bone models, or a combination thereof using computer-aided manufacturing (CAM) techniques as described above.

Range-of-motion models are also generated. The range-of-motion models may be generated by positioning the 3-D bone models relative to one another according to the patient's anatomy and rotating the bone models about one or more known rotational axes, such as the epicondylar axis for a knee joint. This provides the expected ranges-of-motion in flexion-extension, abduction-adduction, and/or internal-external rotation/orientation between the first bone and the second bone. In some embodiments, the range-of-motion models further include an expected laxity between the two bones by simulating the soft tissues attached to or surrounding the bone such as the medial collateral ligament (MCL) and the lateral collateral ligament (LCL).

To perform the first set of simulations (Block 208), a computer is provided having robot simulation software with the following: (i) a kinematic model of the robot; (ii) a virtual model of an end-effector; (iii) the virtual bone models; and (iv) the range-of-motion models. The kinematic model of the robot refers to the configuration of the robot links and joints and their relative motion to one another, which may be described by Denavit-Hartenberg (DH) parameters. A virtual model of the robot or a virtual model representing the links and joints of the robot may also be shown in the robot simulation software. The virtual model of the robot end-effector may be generated using computer-aided design (CAD) techniques known in the art.

Figure 4:
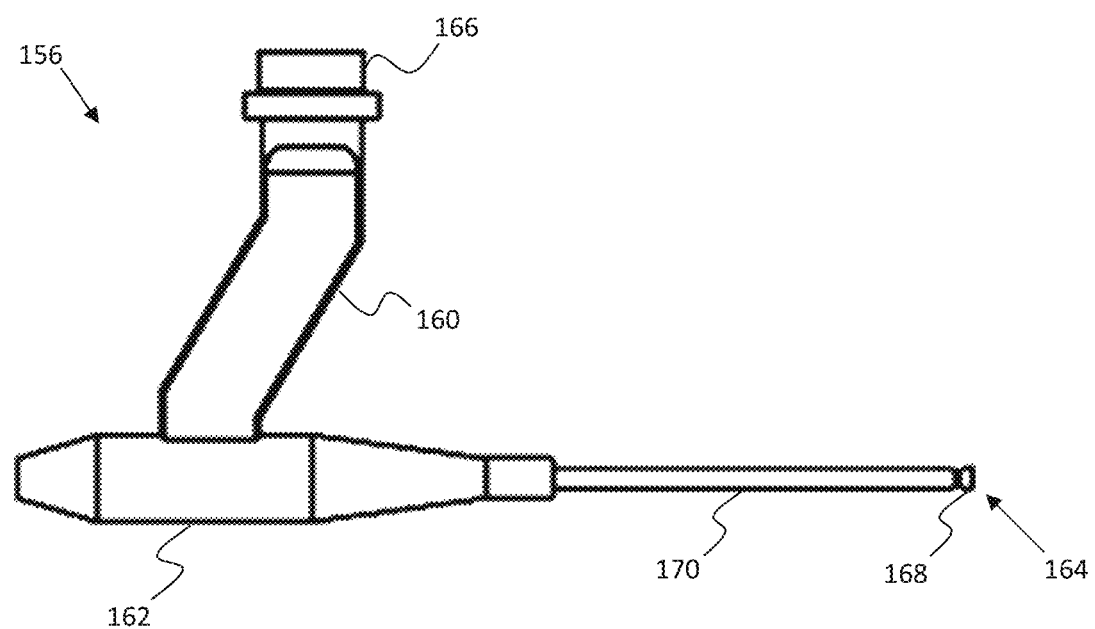
FIG. 4 depicts a prior art end-effector of a robotic system that may be modelled for use with embodiments of the invention.

With reference to FIG. 4, a particular embodiment of a prior art end-effector is shown. The end-effector 156 generally includes an extension arm 160, a housing 162, and a cutting tool 164. The extension arm 160 extends from the housing 162 and is configured to attach the end-effector 156 to a distal flange 166 or coupler of a robotic arm 154. The housing 162 may house a motor or other actuator to rotationally drive the cutting tool 164. The cutter tool 164 may include a shaft having one end connected with the motor or actuator, and a cutting end 168 at the opposing end of the shaft. The cutting end 168 may illustratively be an end-mill, drill bit, or other cutting device capable of removing bone. The end-effector 156 further includes a sleeve 170 that extends from the housing 162 to surround and support the shaft of the cutting tool 164. The robot simulation software further includes the virtual bone models, the range-of-motion models, and the cut-files as generated above. The cut-files may be uploaded into the robot simulation software as part of the virtual bone models, where a user planned the position of the cut-files (e.g., by way of positioning an implant model, or directly) relative to the bone models, which fixes the cut-files position relative to the bone models.

Figure 5A:
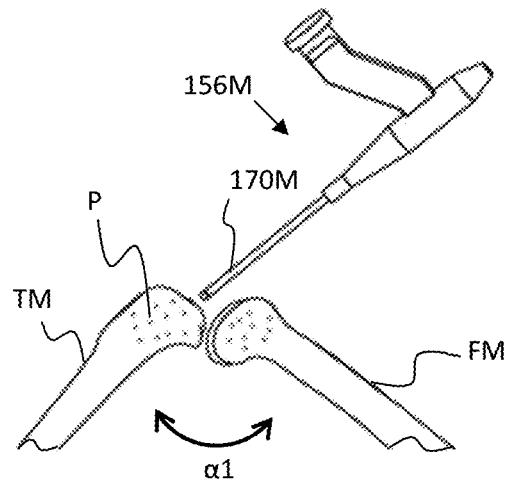
FIG. 5A depicts a simulation of an end-effector executing a cut-file on a bone, where two bones are orientated at a first angle relative to one another in accordance with embodiments of the invention.
Figure 5B:
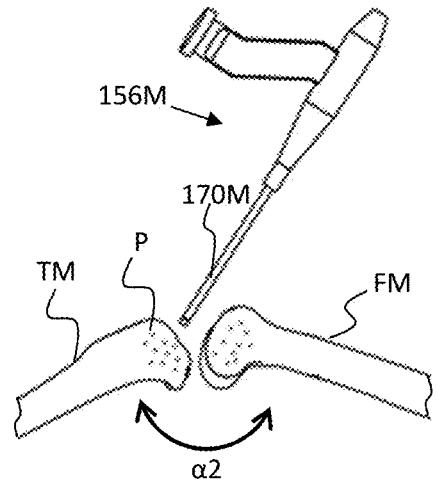
FIGS. 5B and 5C depict a simulation of an end-effector executing a cut-file on a bone, where two bones are orientated at a second angle relative to one another in accordance with embodiments of the invention, where
Figure 5C:
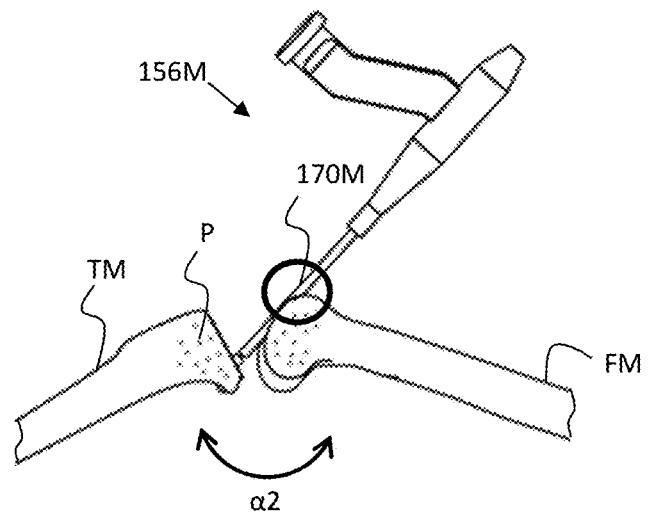

The robot simulation software performs the first set of simulations as described with reference to FIGS. 5A to 5C. FIG. 5A depicts a tibia bone model TM, a femur bone model FM, and an end-effector virtual model 156M, where the tibia bone model TM and femur bone model FM are oriented at a first angle $\alpha 1$. The points P inside the tibia bone model TM and femur bone model FM illustratively represent the points in a cut-file. At angle $\alpha 1$, the software simulates the entirety of the cut-files on the tibia bone model TM and the femur bone model FM to determine if the end-effector can successfully complete the cut-files as characterized by a portion of the end-effector virtual model 156M not inadvertently interfering or colliding with an unintended portion of the tibia bone model TM or the femur bone model FM. In this hypothetical example, at angle $\alpha 1$, no portion of the end-effector 156M inadvertently collided with an unintended portion of the bone models. Once the simulation is completed at angle $\alpha 1$, the bones are re-oriented to a new angle $\alpha 2$ where the simulation is repeated as shown in FIGS. 5B and 5C. FIG. 5B and FIG. 5C show the progression of the end-effector 156M executing the cut-file with the bone models (TM and FM) orientated at angle $\alpha 2$ (i.e., FIG. 5B shows the orientation of the end-effector 156M to remove bone at a first point in the cut-file, and FIG. 5C shows the orientation of the end-effector 156M to remove bone at a second point in the cut-file). In FIG. 5B, it can be seen that no portion of the end-effector 156M inadvertently collided with an unintended portion of bone models, while in FIG. 5C it can be seen that a portion of the end-effector sleeve 170M inadvertently collided with the femur bone model FM (as denoted by the circle) while the end-effector 156M is removing bone on the tibia bone model TM. Therefore, when the bone models are oriented at angle $\alpha 2$, the completion of the cut-file is deemed unsuccessful because in the operating room, if the user were to position the bones at orientation $\alpha 2$ in the workspace, the forces on the end-effector would exceed the threshold force due to the contact with the femur bone and cause a force freeze.

The above simulations are repeated for different orientations as described by the range-of-motion model to complete the first set of simulations. In some embodiments, the orientations may be adjusted by a set value for each simulation. For example, a first simulation with the bone models in full extension, a second simulation for the bone models flexed by 2 degrees, a third simulation for the bone models flexed by 4 degrees, and so on until the bone models reach maximum flexion.

Based on the first set of simulations, the one or more orientations of the bone models (e.g., $\alpha 1$, $\alpha 2$) that had a successful non-collision completion of the cut-file is determined. In particular embodiments, the determined one or more orientations is a range of orientations. For example, the first set of simulations may determine that a range of 20 degrees flexion to 80 degrees flexion results in a successful non-collision completion. These one or more orientations and/or range of orientations are used to complete a second set of simulations.

The second set of simulations are performed on a computer having robot simulation software that is programmed with a kinematic model of the robot to simulate the robot's movements as defined in the cut-file. These simulations are repeated for a plurality of cut-file POSEs in a virtual workspace of the robot to determine where in the workspace the robot can successfully complete the cut-file kinematically as was described with reference to FIGS. 2A to 2C. For example, a first cut-file CF1 and a second cut-file CF2 may be virtually positioned at a first position P1 in the robot workspace 158. At position P1, the cut-files (CF1 and CF2) are simulated over a range of cut-file orientations, where the range of cut-file orientation are now limited to the determined one or more orientations or range of orientations (e.g., 20 degrees to 80 degrees) found in the first set of simulations. That is, at position P1, a first simulation is performed with the cut-files (CF1 and CF2) flexed at 20 degrees, and a then a second simulation is performed with the cut-files (CF1 and CF2) flexed at 30 degrees, and so on up until the cut-files are flexed at 80 degrees.

After the simulations are completed at position P1 over the range of orientations, the cut-files (CF1 and CF2), either simultaneously or separately, are positioned at a new position (e.g., P2, P3, P4) and the process is repeated. For each simulation, the simulation software determines which cut-files had a successful kinematic completion of the cut-file as characterized by: (i) the end-effector 156 capable of reaching all of the trajectory points (or virtual boundaries) along a plurality of cut paths defined in the cutfile, and (ii) the joint positions and velocity limits of the robot arm 154M are within operating range.

From the data acquired from the simulations, a workspace map 180 is generated as shown in FIG. 2B. The feasibility measures and optimal bone placement may be calculated in the same manner as described above.

In the OR, a user is guided to position and orient the bone(s) in the workspace of the robot via a graphical user interface (GUI). The GUI may display the determined optimal placement relative to a representation of the robot to help guide the user in positioning the bones. If the bones are tracked, virtual bone models may be displayed on the GUI, where the position of the virtual bone models relative to a representation of the robot is displayed and updated in real-time as the user positions the actual bones in the workspace. Other guiding mechanisms may include a projected laser in the workspace of the robot, tracked tactile or haptic gloves, holograms, or mechanical hardware (e.g., rods, bars, arms, brackets, frames) that may be attached to the surgical robot to indicate the optimal placement for the bones.

It should be appreciated that the first set of simulations and second set of simulations may be combined into one set of simulations. For example, one set of simulations may determine both a successful non-collision completion of the simulation of a cut-file and a successful kinematic completion of the simulation of a cut-file.

Another method to detect a collision between the end-effector, the robot arm, the bone, and/or a mechanical digitizer attached to a base of the robot may include the following. Collision detection algorithms may be used while performing the simulations described in FIG. 1. A collision detection algorithm may determine if a portion of the end-effector interferes or collides with an unintended point or cut path in the cut-file for each cut-file POSE. If a collision is detected, that cut-file POSE is labeled as invalid (or unsuccessful). The invalid POSEs may be incorporated into the above feasibility calculations to determine optimal bone placements. Likewise, the mechanical digitizer and robot arm may be modeled in a similar manner to determine if any collisions occur between the end-effector, the digitizer and/or robot arm for each cut-file POSE.

Further, the methods (100 and 200) described herein may be used for additional purposes. In a particular embodiment, the methods (100 and 200) may be used to adjust the cut-files (e.g., position on the bone models, the POSE or number of cut-paths, position of points, position of planes, position of boundaries) for certain patient's with limited range of motion (ROM). If there is a minimal ROM, then the cut-file can be adjusted to make the best cuts possible. For example, if it is determined from the simulations that the end-effector will collide with a patient's bone because of their limited ROM, the cut-files may be adjusted to cut as much bone as possible without causing a collision. In a specific embodiment, the methods (100 and 200) can provide the surgeon with an expectation of what can and cannot be cut for each patient case and make appropriate preparations therefore. For instance, the simulations may determine that the end-effector can only cut one portion of bone, and is inhibited from reaching other portions due to collisions with unintended portions of bone. The surgeon can then make the appropriate preparations to cut the remaining bone (i.e. the bone the end-effector cannot cut) using manual instruments.

Surgical System

Figure 6:
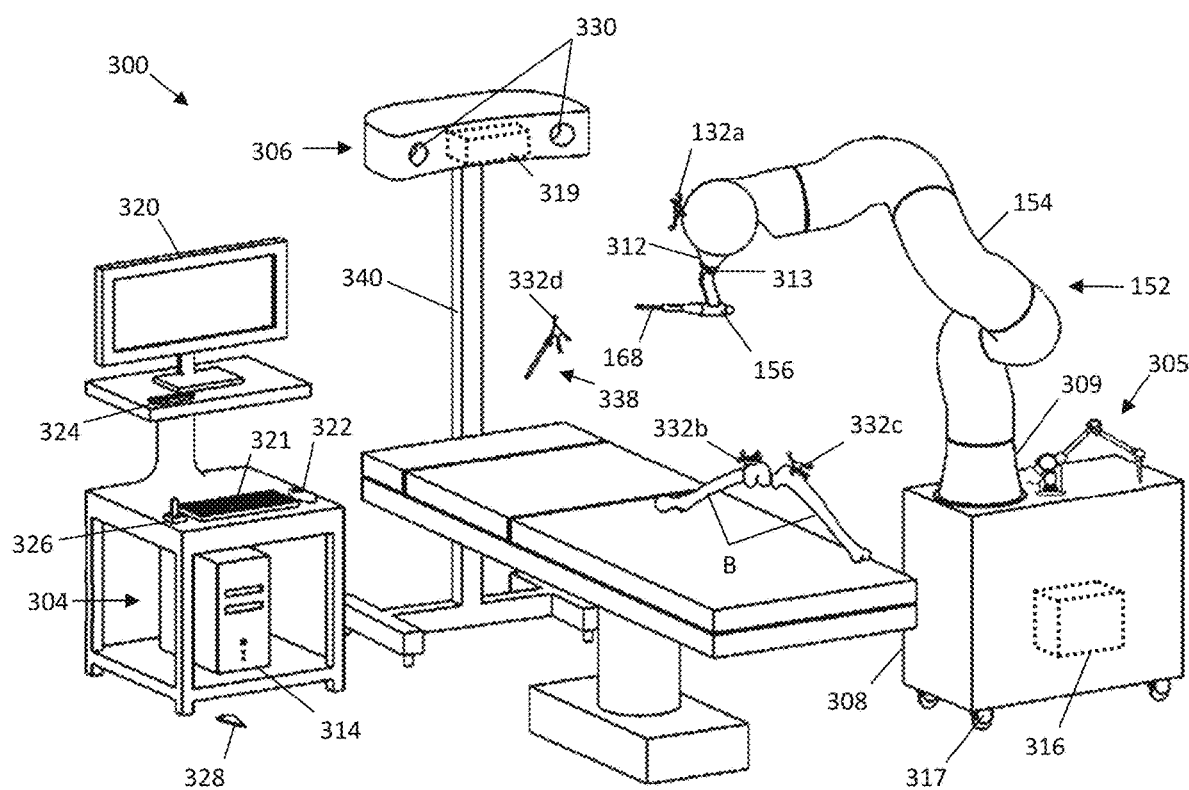
FIG. 6 depicts a robotic surgical system in accordance with embodiments of the invention.

With reference to FIG. 6, an example of a computer-assisted surgical system 300 in the context of an operating room (OR) is shown for implementing embodiments of the invention. The surgical system 300 may generally include a surgical robot 152, a computing system 304, a mechanical digitizer arm 305 and/or a non-mechanical tracking system 306 (e.g., an optical tracking system, an electro-magnetic tracking system), and a rollable or handheld digitizer 338.

The surgical robot 152 includes in some inventive embodiments, a movable base 308, a manipulator arm 154 connected to the base 308, an end-effector flange 312 located at a distal end of the manipulator arm 154, and an end-effector assembly 156 removably attached to the flange 312 by way of an end-effector mount/coupler 313. The end-effector assembly 156 holds and/or operates an end-effector tool 168 that interacts with a portion of a patient's anatomy. The base 308 includes a set of wheels 317 to maneuver the base 308, which may be fixed into position using a braking mechanism such as a hydraulic brake. The base 308 may further include an actuator 309 to adjust the height of the manipulator arm 154. The manipulator arm 154 includes various joints and links to manipulate the tool 168 in various degrees of freedom. The joints are illustratively prismatic, revolute, spherical, or a combination thereof.

The computing system 304 generally includes a planning computer 314; a device computer 316; an optional tracking computer 319 if a tracking system 306 is present; and peripheral devices. The planning computer 314, device computer 316, and tracking computer 319, may be separate entities, single units, or combinations thereof depending on the surgical system. The peripheral devices allow a user to interface with the robotic surgical system 300 and includes in some inventive embodiments: one or more user-interfaces, such as a display or monitor 320; and user-input mechanisms, such as a keyboard 321, mouse 322, pendent 324, joystick 326, foot pedal 328, or the monitor 320 in some inventive embodiments may have touchscreen capabilities.

The planning computer 314 contains hardware (e.g., processors, controllers, and memory), software, data and utilities that are in some inventive embodiments dedicated to the planning of a surgical procedure, either pre-operatively or intra-operatively. This may include reading medical imaging data, segmenting imaging data, constructing three-dimensional (3D) virtual models, storing computer-aided design (CAD) files, providing various functions or widgets to aid a user in planning the surgical procedure, modeling the bones range-of-motion, executing finite element analysis, determining stability regions, and generating surgical plan data. The final surgical plan includes operational data for modifying a volume of tissue that is defined relative to the anatomy, illustratively including: a set of instructions (e.g., points, cut paths, velocities) in a cut-file to autonomously modify the volume of bone; a set of virtual boundaries defined to haptically constrain a tool within the defined boundaries to modify the bone; a set of planes or drill holes to drill pins in the bone; or a graphically navigated set of instructions for modifying the tissue. In particular inventive embodiments, the operational data specifically includes a cut-file for execution by a surgical robot to autonomously or automatically modify the volume of bone, which is advantageous from an accuracy and usability perspective. The data generated from the planning computer 314 may be transferred to the device computer 316 and/or tracking computer 319 through a wired or wireless connection in the operating room (OR); or transferred via a non-transient data storage medium (e.g., a compact disc (CD), a portable universal serial bus (USB) drive).

The device computer 316 in some inventive embodiments is housed in the moveable base 308 and contains hardware (e.g., controllers), software, data and utilities that are preferably dedicated to the operation of the surgical robot 152. This may include surgical device control, robotic manipulator control, the processing of kinematic and inverse kinematic data, the execution of registration algorithms, the execution of calibration routines, the execution of surgical plan data, the execution of operational data, coordinate transformation processing, providing workflow instructions to a user, utilizing position and orientation (POSE) data from the tracking system 306, and reading data received from the mechanical arm 305.

The optional tracking system 306 of the surgical system 300 may be an optical tracking system as described in U.S. Pat. No. 6,061,644. The optical tracking system includes two or more optical receivers 330 to detect the position of tracking arrays (332a, 332b, 332c), where each tracking array (332a, 332b, 332c) has a unique arrangement of fiducial markers, or a unique transmitting wavelength/frequency if the markers are active LEDs. The tracking system 306 may be built into a surgical light, located on a boom, a stand 340, or built into the walls or ceilings of the OR. The tracking system computer 319 includes in some inventive embodiments, tracking hardware, software, data and utilities to determine the POSE of objects (e.g., bones B, rollable or handheld digitizer 338, and surgical robot 152) in a local or global coordinate frame. The POSE of the objects is collectively referred to herein as POSE data, where this POSE data may be communicated to the device computer 316 through a wired or wireless connection. Alternatively, the device computer 316 may determine the POSE data using the position of the fiducial markers detected from the optical receivers 330 directly.

The POSE data is used by the computing system 304 during the procedure to update the POSE and/or coordinate transforms of the bone B, the surgical plan, and the surgical robot 152 as the manipulator arm 154 and/or bone B move during the procedure, such that the surgical robot 152 can accurately execute the surgical plan. In another embodiment, the surgical system 300 does not include a tracking system 306, but instead employs a mechanical arm 305, and a bone fixation and monitoring system that fixes the bone directly to the surgical robot 152 and monitors bone movement as described in U.S. Pat. No. 5,086,401.

Other Embodiments

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the described embodiments in any way. Rather, the foregoing detailed description will provide those skilled in the art with a convenient roadmap for implementing the exemplary embodiment or exemplary embodiments. It should be understood that various changes may be made in the function and arrangement of elements without departing from the scope as set forth in the appended claims and the legal equivalents thereof.

The invention claimed is:

1. A method for determining a location for one or more bones in a workspace of a robot comprising an end-effector, the method executed on a computing system comprising one or more processors and executing software comprising a kinematic model of the robot and a cut-file, the method comprising:
    simulating robotic movements of a virtual end-effector during robot execution of the cut-file at a first virtual bone location within a virtual workspace of the robot;
    simulating robotic movements of the virtual end-effector during robot execution of the cut-file for at least a second virtual bone location within the virtual workspace of the robot,
    simulating robotic movements of the virtual end-effector during robot execution of a second cut-file for a third virtual bone location within the workspace of the robot;
    simulating robotic movements of the virtual end-effector during robot execution of the second cut-file for at least a fourth virtual bone location within the workspace of the robot, wherein the movements are simulated with simulation software using the kinematic model of the robot;
    determining, for each virtual bone location, if the simulated robotic movements of the virtual end-effector during robot execution of the cut-file or the second cut-file meets predetermined criteria;
    identifying at least one optimal virtual bone location based on a comparison of the predetermined criteria that was met for one virtual bone location compared to at least one other virtual bone location; and
    providing feedback in the operating room for positioning the one or more bones in the workspace of the robot at a location corresponding to at least one optimal virtual bone location.

2. The method of claim 1 wherein the simulating, repeating, and determining steps are executed on a computer comprising a processor, simulation software, and a data storage component storing a kinematic model of the robot.

3. The method of claim 1 further comprising repeating the simulation for a first plurality of cut-file orientations at the first location.

4. The method of claim 3 further comprising repeating the simulation for a second plurality of cut-file orientations at the second location.

5. The method of claim 1 where the predetermined criteria comprises at least one of: (i) the end-effector reaching points defined in the cut-file; (ii) the end-effector reaching boundaries defined in the cut-file; (iii) joint positions of the robot are within operating range; or (iv) velocity limits of the robot are within operating range.

6. The method of claim 1 wherein the predetermined criteria comprises the end-effector reaching all points defined in the cut-file or all boundaries defined in the cut-file.

7. The method of claim 1 wherein the cut-file is generated based on at least one of: (i) a geometry of an implant; (ii) a geometry of the one or more bones; (iii) a planned position for the implant relative to the one or more bones; or (iv) a combination thereof.

8. The method of claim 1 wherein a bone model of the one or more bones is associated with the cut-file, wherein the cut-file is positioned at a predetermined location relative to the bone model.

9. The method of claim 8 wherein the predetermined location corresponds to a planned location for an implant with respect to the one or more bones.

10. The method of claim 1 further comprising saving at least one cut-file location that meets the predetermined criteria for positioning the one or more bones in an operating room.

11. The method of claim 10, wherein a bone model of the one more bones is associated with the cut-file, wherein the cut-file is positioned at predetermined location relative to the bone model, and wherein the method further comprises displaying, on a graphical user interface, the bone model at a saved cut-file location relative to a representation of at least one of the robot or a workspace of the robot.

12. The method of claim 1 further comprising repeating the simulation for three or more locations of the cut-file, and for each location repeating the simulation for a plurality of cut-file orientations.

13. The method of claim 12 further comprising generating a workspace map based on data acquired from the simulations.

14. The method of claim 13 wherein the workspace map comprises a plurality of data points, wherein each data point corresponds to a cut-file location within the workspace, and wherein the data in each data point comprises information related to a cut-file location or a cut-file orientation meeting the predetermined criteria.

15. The method of claim 1 wherein a first bone model of a first bone from the one or more bones is associated with the cut-file and a second bone model of a second bone from the one or more bones is associated with the second cut-file, wherein the first bone and second bone form a joint.

16. The method of claim 15 wherein the first bone is a femur and the second bone is a tibia.

17. The method of claim 15 further comprising:
repeating the simulation of the cut-file for a first plurality of cut-file orientations at the first location; and
repeating the simulation of the second cut-file for a second plurality of cut-file orientations at the third location;
wherein the first plurality of cut-file orientations with respect to the second plurality of cut-file orientations correspond to a range-of-motion of the joint.

18. The method of claim 1 wherein the at least one optimal virtual bone location is a virtual bone location having more predetermined criteria met compared to another virtual bone location.

19. The method of claim 1 further comprising positioning in an operating room prior to surgery the one or more bones in the workspace of the robot according to the at least one optimal virtual bone location and based on the simulation using the kinematic model.

* * * * *